United States Patent [19]

Castaldi et al.

[11] Patent Number: 4,582,930

[45] Date of Patent: Apr. 15, 1986

[54] PROCESS FOR THE PREPARATION OF OPTICALLY ACTIVE ALPHA-ARYLALKANOIC ACIDS

[75] Inventors: Graziano Castaldi, Briona; Claudio Giordano, Vicenza; Fulvio Uggeri, Codogno, all of Italy

[73] Assignee: Zambon S.p.A., Vicenza, Italy

[21] Appl. No.: 704,407

[22] Filed: Feb. 22, 1985

[30] Foreign Application Priority Data

Feb. 24, 1984 [IT] Italy ............................... 19783 A/84

[51] Int. Cl.$^4$ ............................................. C07C 63/36
[52] U.S. Cl. ....................................... 562/490; 560/56; 560/100; 562/465; 562/466; 562/493
[58] Field of Search ............... 562/490, 466, 465, 493; 560/100, 56

[56] References Cited

U.S. PATENT DOCUMENTS 4,356,188 10/1982 Pacheco et al. ..................... 514/569
4,501,913 2/1985 Giordano ............................. 562/490

Primary Examiner—Paul J. Killos
Attorney, Agent, or Firm—Cushman, Darby & Cushman

[57] ABSTRACT

A process is disclosed for the preparation of optically active alpha-arylalkanoic acids, consisting in the rearrangement of optically active alpha-(haloalkyl)-arylketals and in submitting to hydrolysis the so-obtained esters of alpha-arylalkanoic acids.

The rearrangement reaction is carried out under neutral or slightly alkaline conditions in a polar protic medium.

7 Claims, No Drawings

PROCESS FOR THE PREPARATION OF OPTICALLY ACTIVE ALPHA-ARYLALKANOIC ACIDS

The present invention relates to a process for the synthesis of optically active alpha-arylalkanoic acids, and more particularly it relates to a process for preparing such acids by means of the rearrangement of suitable ketals under neutral or slightly alkaline conditions in a polar protic medium, then submitting to hydrolysis the ester obtained by rearrangement.

Many alpha-arylalkanoic acids are known due to their pharmaceutical properties (anti-inflammatory agents, analgesics).

Among these, 2-(4-isobutylphenyl)-propionic acid known as Ibuprofen, 2-(3-phenoxyphenyl)-propionic acid known as Fenoprofen, 2-(2-fluoro-4-biphenylyl)-propionic acid known as Flurbiprofen, 2-[4-(2-thienyl-carbonyl)-phenyl]-propionic acid known as Suprofen, 2-(6-methoxy-2-naphthyl)-propionic acid, whose d-isomer is known as Naproxen, and still others, may be mentioned.

Another group of alpha-arylalkanoic acids are useful as intermediates for the preparation of pyrethroid insecticides, among these are 2-(4-chlorophenyl)-3-methyl-butyric acid, and 2-(4-difluoromethoxyphenyl)-3-methyl-butyric acid.

Many alpha-arylalkanoic acids have at least one asymmetry centre, in this case the carbon atom in the alpha position with respect to the carboxyl group, and exist therefore in the form of two stereoisomers. Often, to one of the two isomers a decidedly higher biological activity is associated.

A particularly evident example is given by 2-(6-methoxy-2-naphthyl)-propionic acid, whose d-isomer (Naproxen) shows pharmacological properties definitely higher than those of the l-isomer and of the racemic mixture.

Due to this reason, it is useful that a stereoselective process be available, leading to the formation of desired optical isomer in a substantially pure form. In European Patent Application No. 81993 to Syntex, claiming the priority of U.S. patent application Ser. No. 329,672 filed on Dec. 11, 1981, a stereoselective process is disclosed for preparing optically active ketones of formula

wherein Ar=aryl, R$_1$=alkyl or cycloalkyl, and Z represents a leaving group, or a group capable of being transformed into a leaving group.

The preferred leaving groups are: halogen atoms, or a group of formula

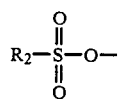

wherein R$_2$=alkyl, cycloalkyl, alkenyl, alkynyl, aryl or arylalkyl.

The preparation of ketones of formula (A) is carried out by reacting an organometallic compound, such as an aryl-magnesium halide with an optically active acyl halide, or by similar methods. According to what reported in European Patent Application No. 81993, the optically active ketones of formula (A) are then transformed into the optically active ketals of formula

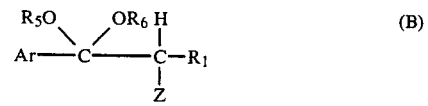

wherein Ar, R$_1$ and Z have the meanings indicated above, R$_5$ and R$_6$ are alkyl, aryl or arylalkyl, or together are a C$_2$-C$_8$ alkylene.

From what reported in European Patent Application No. 81993, it is drawn that the preparation of ketals (B) from the ketones (A) is carried out by means of traditional methods for preparing ketals from ketones (see e.g. the disclosure from page 28, line 4 to page 29, line 20). The optically active ketals of formula (B) are subsequently transformed by rearrangement into the optically active alpha-arylalkanoic acids (or into the ester, orthoester or amide derivatives thereof) of formula

wherein Ar and R$_1$ have the meanings mentioned above.

As it results clearly from the specification of the above mentioned European patent application, the rearrangement step is carried out according to one of the methods known to the date of filing of the priority application of the U.S.A. (Dec. 11, 1981). In fact, at page 29, line 24–foll., it is reported that when in the optically active ketals Z is a halogen, the rearrangement is carried out accordingly to what disclosed in European Patent Application No. 34871 published on Sept. 2, 1981.

An alternative process, when Z is halogen, is the one disclosed in U.K. Patent Application No. 2042543 published on Sept. 24, 1980 (see European Patent Application No. 81993, pag. 30, lines 28–foll.).

When Z is a leaving group of formula R—SO$_2$—O—, the rearrangement is carried out under conditions similar or analogous to those described in the paper Tetrahedron Letters 22 (43), 4305-8,(1981), quoted at page 3, lines 30-34 of European Patent Application No. 81993.

The above mentioned known methods for the rearrengement of ketals into alpha-arylalkanoic acids, even if not specifically referring to the rearrangement of optically active ketals, describe the reaction starting from ketals of not specified isomerism.

From the specification of European patent application No. 81993, it is drawn that the known methods described in the above mentioned references can be transferred, without changes, to the rearrangement of optically active ketals of formula (B) (or of the other analogous ketals described in European Patent Application No. 81993).

European Patent Application No. 67698 to Sagami Chemical Research Center published on Dec. 22, 1982 discloses and claims a process for the preparation of optically active ketones of formula practically analogous to the above reported formula (A), and shows how such ketones can be transformed into ketals of formula analogous to the formula (B) reported above (wherein however Z is only a sulphonyloxy group) and then rearranged into alpha-arylalkanoic acids.

In our preceding Italian Patent Application No. 22760 A/82 filed on Aug. 6, 1982, a process has been disclosed for preparing alpha-arylalkanoic acids by means of the rearrengement of (alpha-haloalkyl)-aryl-ketals in a neutral or slightly alkaline medium, and in the presence of a polar protic medium (e.g., water, alcohols, formamide, acetamide, and so on). Optionally, the reaction may be carried out in the presence of an inert diluent such as dimethylformamide, dimethylsuplhoxide, toluene, acetone, and so on.

In another Italian Patent Application of ours, No. 19930 A/83 filed on Mar. 7, 1983, we have disclosed novel ketals useful to give alpha-arylalkanoic acids by rearrangement.

The process disclosed in Italian Patent Application No. 22760 A/82 shows important advantages over the other rearrangement processes above mentioned. The main ones among such advantages may be summarized in the fact that the reaction does not require the presence of Lewis acids as catalysts (according to the European Patent Application No. 34871), in fact the main Lewis acids are heavy metal halides, and these are not compatible with products intended for pharmaceutical use, and in the fact that the starting products are halo-ketals, and hence it is not necessary to prepare the sulphonyloxy-ketals (according to the work published on Tetrahedron Letters or according to European Patent Application No. 67698).

We have now found and is the object of the present invention, a process for preparing optically active alpha-arylalkanoic acids, consisting in rearranging (alpha-haloalkyl)-aryl-ketals in neutral or slightly alkaline conditions in the presence of a polar protic medium, and in submitting to hydrolysis the esters obtained from the rearrangement reaction. The process being the object of the present invention, when compared to the process disclosed in European Patent Application No. 34871 shows the same advantages of Italian Patent Application No. 22760 A/82, the main one among them consisting in the fact that the use of heavy-metal salts as rearrangement catalysts is avoided.

When compared to the process disclosed in European Patent Application No. 81993 (using for the rearrangement the conditions as disclosed in European Patent Application No. 34871), the process according to the present invention shows the advantage of not requiring the use of heavy-metal salts as rearrangement catalysts, and in this case the use of heavy metals in an even worse factor, in that the process of European Patent Application No. 81993 directly provides optically active alpha-arylalkanoic acids for direct pharmaceutical use.

Moreover, surprisingly, the process being the object of the present invention provides alpha-arylalkanoic acids of greater optical purity than those obtained by rearranging the same starting products according to what disclosed in European Patent Application No. 81993, and precisely by operating under the conditions disclosed by European Patent Application No. 34871. A scheme representing an aspect of the process being the object of the present invention is shown by the following reactions:

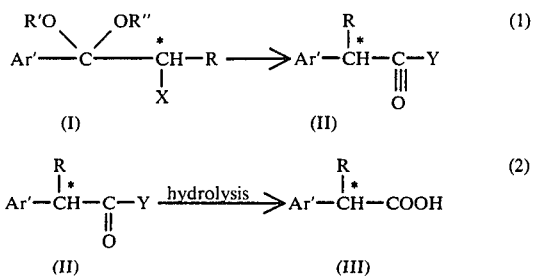

wherein

Ar' represents an aromatic group comprising (a) a phenyl substituted with one or two substituents selected from halogen atoms, $C_1$–$C_6$ alkyl, $C_1$–$C_4$ alkoxy, $C_2$–$C_4$ alkenyloxy, phenyl, phenoxy, dichloro-phenoxy, dichloroanilino, difluoromethoxy, benzoyl, indolyl, dihydropyrrolyl, thienoyl; (b) a naphthyl substituted with one or two substituents selected among halogen atoms and $C_1$–$C_4$ alkoxy; (c) a pyrrolyl substituted with one or two substituents selected among $C_1$–$C_4$ alkyl and $C_1$–$C_4$ alkylphenyl; (d) chlorocarbazolyl; (e) chlorophenyl-benzoxazolyl; (f) thiazolyl substituted with phenyl or chlorophenyl, and (g) thienyl.

R' and R", equal to or different from each other, represent a straight or branched $C_1$–$C_{12}$ alkyl, or a straight or branched $C_2$–$C_{12}$ alkenyl; or R' and R" together represent a saturated or unsaturated, straight or branched $C_2$–$C_{12}$ alkylene, so as to form with the oxygen atoms and the carbon atom to which they are bonded, a ring of from 5 to 7 atoms;

R represents a straight or branched $C_1$–$C_6$ alkyl, or a $C_3$–$C_7$ cycloalkyl;

X represents a chlorine, bromine or iodine atom;

the asterisk (*) marks the asymmetric carbon atom;

the —CO—Y group represents a group supplying a carboxyl group by hydrolysis.

Preferably, the —CO—Y group represents an ester group of formula —CO—OY', wherein Y' in general is an alkyl when R' and R" are alkyls, or is a substituted alkyl or alkenyl when R' and R" together form a saturated or unsaturated alkylene; the particular substituent of Y' will depend on the reaction medium.

Specific meanings for the above shown substituents comprise for Ar' 4-isobutylphenyl, 4-chlorophenyl, 4-difluoromethoxy-phenyl, 6-methoxy-2-naphthyl;

for R' and R" separately methyl or ethyl;

for R' and R" jointly the groups —$CH_2$—$CH_2$—, —$CH_2$—$CH_2$—$CH_2$—, —$CH_2$—$C(CH_3)_2$—$CH_2$—, —$CH_2$—CH=CH—$CH_2$—;

for X chlorine and bromine;

for R methyl, ehtyl, n.propyl, isopropyl.

In a specific embodiment thereof, the invention comprises the preparation of d isomer of 2-(6-methoxy-2-naphthyl)-propionic acid known as Naproxen, according to the reactions 1 and 2 reported above, starting from a compound of formula

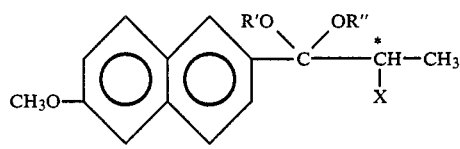

wherein R', R" and X have the previously mentioned meanings, and in particular the specific meanings reported above.

The starting products of the process being the object of the present invention, and precisely the optically active ketals of formula (I), are prepared according to methods per se known, and in particular by means of conventional techniques of ketalization of optically active ketones. Depending on the selected type of ketalization, it will be possible to have the preservation of the configuration, with respect to the initial optically active ketone, of the inversion of the configuration.

The optically active ketones necessary for the preparation of ketals of formula (I) can be prepared by means of the Friedel-Crafts reaction, as disclosed in European Patent Application No. 67698, or following the Grignard, and similar reactions, as disclosed in European Patent Application No. 81993. Of course, the present invention is not to be intended as being limited to the case wherein the optically active ketals are prepared as previously briefly mentioned, but it comprises the rearrangement of optically active (alpha-haloalkyl)-aryl-ketals independently from the methods by which these latter are prepared.

As previously mentioned, the process being the object of the present invention is formed by a rearrangement step, and a subsequent hydrolysis step.

The rearrangement of optically active (alpha-haloalkyl)-aryl-ketals is carried out under neutral or slightly alkaline conditions, in the presence of a polar protic medium.

The neutral or slightly alkaline conditions are obtained by using organic or inorganic weak bases or buffers.

Examples of weak bases useful are aliphatic or aromatic tertiary amines, alkaline or alkaline-earth salts of weak acids such as sodium bicarbonate, calcium carbonate, potassium acetate, etc.

The polar protic medium wherein the reaction occurs comprises water, alcohols and glycols or their mixtures.

As specific examples of alcohols, methanol, ethanol, butanol, isobutanol, sec.butanol, 2-decanol, allyl alcohol, and more generally primary, secondary or tertiary $C_1$–$C_{12}$ alcohols, may be mentioned. Similarly, specific examples of glycols comprise ethylene glycol, 1,2-propanediol, 1,3-propanediol, 2,2-dimethyl-1,3-propane-diol, 1,10-decanediol, cis-2-butene-1,4-diol, and in general straight or branched $C_2$–$C_{12}$ diols.

In general, a more lipophilic medium (long-chain alcohol or diol) is selected to the purpose of dissolving lower-polarity ketals. The reaction is normally effected at temperatures comprised within the range of from 80° to 200° C.

The reaction time depends on several factors, such as the reactivity of the starting ketal, the polarity of the medium, and the reaction temperature, and may vary from a few minutes, to about 12 hours.

At the end of the rearrangement step, the reaction mixture is treated according to conventional techniques for isolating the thus-obtained compound of formula (II).

The hydrolysis step is then carried out, it too being effected following conventional techniques, mainly with acidic catalysis, thus obtaining the optically active alpha-aryl-alkanoic acid, with a high purity. In a practical embodiment thereof, the process according to the present invention is carried out by introducing into the reaction vessel the optically active ketal, an amount of weak base or of buffer as to assure a neutral or slightly alkaline pH value, and such an amount of polar protic substance sufficient for at least partially dissolving the ketal. The reaction mixture is then heated under stirring to a temperature of from 80° to 200° C., and the course of the reaction is followed by means of conventional techniques (GLC, TLC or IR spectroscopy). At the end of the rearrangement reaction, the reaction mixture is poured into water or diluted, the reaction product (compound of formula [II]) is extracted with a suitable organic solvent, and isolated.

Then, the hydrolysis of the compound of formula (II) is carried out according to conventional techniques, but preferably by acidic catalysis. Alternatively, the hydrolysis of the ester may be effected without isolating it, by adding an aqueous mineral acid to the mixture resulting from the rearrangement reaction.

To the purpose of better illustrating the invention, the following Examples are now given.

EXAMPLE 1

A mixture of (S) 2-bromo-1,1-dimethoxy-1-(6-methoxy-2-naphthyl)-propane (3.39 g; 10 mmol) (prepared as described in Example 22, pag 57, of European Patent Application No. 81,993), potassium acetate (1.2 g; 12 mmol), 1,2-ethyleneglycol (40 ml) is stirred at the temperature of 125° C. for 8 hours.

After cooling to 25° C., the mixture is diluted with diethyl ether, and filtered. The organic solution is then washed with water and dried on anhydrous sodium sulphate.

· The solvent is eliminated by evaporation under reduced pressure, and the residue is diluted with dimethoxyethane (30 ml) and 10N hydrochloric acid (30 ml).

The mixture is maintained at 50° C. for 24 hours, and is then diluted with water and extracted with diethyl ether.

The combined organic phases are washed with water, and dried on anhydrous sodium sulphate.

After evaporation of the solvent under reduced pressure, (S)-2-(6-methoxy-2-naphthyl)-propionic acid (d isomer) is obtained, having an optical purity reflecting the purity of the starting product. Yield 82%; m.p. 155°–156° C.

EXAMPLE 2

A mixture of (+) (S) 2-(1'-bromethyl)-2-(6'-methoxy-2'-naphthyl)-1,3-dioxolane (2.68 g; 0.008 mol), disodium phosphate (1.36 g; 0.0095 mol), monopotassium phosphate (1.44 g; 0.01 mol) and ethylene glycol (40 ml) is heated to 125° C. for 16 hours.

By following the procedure of Example 1, there is obtained (+) (S) 2-(6-methoxy-2-naphthyl)-propionic acid (1.25; 0.005 mol). Yield, 62.5%; m.p. 155°–156° C.

EXAMPLE 3

A mixture of (+) (S) 2-(1'-bromoethyl)-2-(6'-methoxy-2'-naphthyl)-1,3-dioxolane (13.48 g; 0.042 mol), potassium bicarbonate (6 g; 0.06 mol) and ethylene glycol (200 ml) is heated to 125° C. for 18 hours. By following the procedure of Example 1, there is obtained (+) (S) 2-(6-methoxy-2-naphthyl)-propionic acid (6.91 g; 0.03 mol). Yield, 71.5%; m.p. 155°–156° C.

EXAMPLE 4

A mixture of (+) (S) 2-(1'-bromoethyl)-2-(6'-methoxy-2'-naphthyl)-1,3-dioxane (3.51 g; 0.01 mol), potassium acetate (1.2 g; 0l012 mol) and 1,3-propanediol (50 ml) is heated to 125° C. for 8 hours. By following the procedure of Example 1, there is obtained (+) (S) 2-(6-methoxy-2-naphthyl)-propionic acid (2.25 g; 0.0098 mol). Yield, 98%; m.p. 155°-156° C.

We claim:

1. Process for the preparation of optically active alpha-arylalkanoic acids, consisting in submitting to rearrangement reaction the corresponding optically active (alpha-haloalkyl)-aryl-ketals in neutral or slightly alkaline conditions, in the presence of a polar protic medium, and in submitting to hydrolysis the product obtained by the rearrangement.

2. Process for the preparation of alpha-arylalkanoic acids as claimed in claim 1, applied to the synthesis of (S) 2-(6-methoxy-2-naphthyl)propionic acid (Naproxen).

3. Process for the preparation of (S) 2-(6-methoxy-2-naphthyl)-propionic acid as claimed in claim 2, characterized in that as starting product the suitable isomeric form is used of an optically active ketal of formula

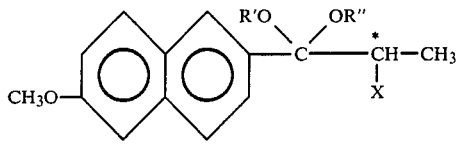

wherein

R' and R", equal to or different from each other, represent a straight or branched $C_1$-$C_{12}$ alkyl or a straight or branched $C_2$-$C_{12}$ alkenyl; or R' and R" together represent a saturated or unsaturated, straight or branched $C_2$-$C_{12}$ alkylene, so as to form with the oxygen atoms and the carbon atom to which they are bonded, a ring of from 5 to 7 atoms;

X represents a chlorine, bromine or iodine atom.

4. Process for the preparation of (S)-2-(6-methoxy-2-naphthyl)-propionic acid as claimed in claim 2, characterized in that as starting product the suitable isomeric form is used of an optically active ketal of formula

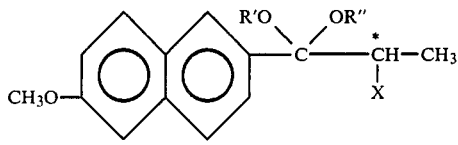

wherein

R' and R" independently represent methyl or ethyl, or together they represent a group selected from —$CH_2$—$CH_2$—, —$CH_2$—$CH_2$—$CH_2$, —$CH_2$—$C(CH_3)_2$—$CH_2$—, —$CH_2$—$CH$=$CH$—$CH_2$—;

X represents a chlorine or bromine atom.

5. Process for the preparation of optically active alpha-arylalkanoic acids as claimed in claim 1, characterized in that the rearrangement reaction is carried out at temperature comprised within the range of from 80° to 200° C.

6. Process for the preparation of optically active alpha-arylalkanoic acids as claimed in claim 1, characterized in that the reaction medium is made neutral or slightly alkaline by means of an aliphatic or aromatic tertiary amine, of an alkaline or alkaline-earth salt of a weak acid, or of a buffer.

7. Process for the preparation of optically active alpha-arylalkanoic acids as claimed in claim 1, characterized in that the polar protic medium is water, $C_1$-$C_{12}$ alcohols, $C_2$-$C_{12}$ glycols, or mixtures thereof.

* * * * *